(12) United States Patent
Takayama et al.

(10) Patent No.: US 9,933,447 B2
(45) Date of Patent: Apr. 3, 2018

(54) AUTOMATIC ANALYZING DEVICE

(71) Applicant: HITACHI HIGH-TECHNOLOGIES CORPORATION, Tokyo (JP)

(72) Inventors: Hiroyuki Takayama, Tokyo (JP); Kazuhiro Nakamura, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 170 days.

(21) Appl. No.: 14/784,359

(22) PCT Filed: Apr. 3, 2014

(86) PCT No.: PCT/JP2014/059889
§ 371 (c)(1),
(2) Date: Oct. 14, 2015

(87) PCT Pub. No.: WO2014/171346
PCT Pub. Date: Oct. 23, 2014

(65) Prior Publication Data
US 2016/0061852 A1    Mar. 3, 2016

(30) Foreign Application Priority Data

Apr. 18, 2013 (JP) ................................. 2013-087413

(51) Int. Cl.
*G01N 35/00* (2006.01)
*G01N 35/04* (2006.01)
(Continued)

(52) U.S. Cl.
CPC ............... *G01N 35/04* (2013.01); *B08B 3/08* (2013.01); *G01N 21/03* (2013.01);
(Continued)

(58) Field of Classification Search
CPC .................................................. G01N 35/0092
See application file for complete search history.

(56) References Cited

U.S. PATENT DOCUMENTS

| 4,785,407 A | 11/1988 | Sakagami |
| 2004/0185549 A1 | 9/2004 | Fujita et al. |

(Continued)

FOREIGN PATENT DOCUMENTS

| EP | 0 289 789 A1 | 11/1988 |
| JP | 63-033662 A | 2/1988 |

(Continued)

OTHER PUBLICATIONS

Hiramatsu, Sep. 1999, JP 11-258246, English machine translation.*

(Continued)

*Primary Examiner* — Jason Ko
(74) *Attorney, Agent, or Firm* — Mattingly & Malur, PC

(57) ABSTRACT

A rinse mechanism rinses reaction cuvettes with first and second detergents. An R1 reagent pipetting mechanism 8 rinses the reaction cuvettes that have been rinsed by the rinse mechanism with a special detergent. A counting unit counts and stores in a storage unit a use frequency of each reaction cuvette for a specific reagent item. A determining unit determines whether the counted use frequency exceeds a predetermined threshold N1. A control unit controls the R1 reagent pipetting mechanism such that, in a case where the counted use frequency exceeds the predetermined threshold N1, the reaction cuvettes, which have exceeded the predetermined threshold N1, are soaked with the special detergent only for a period equal to or less than a value derived by multiplying a pipetting cycle time, which indicates a period when a sample is pipetted, by the total number of reaction cuvettes and a predetermined integer.

9 Claims, 7 Drawing Sheets

(51) Int. Cl.
*B08B 3/08* (2006.01)
*G01N 21/03* (2006.01)

(52) U.S. Cl.
CPC . *G01N 35/0092* (2013.01); *G01N 2035/0437* (2013.01); *G01N 2035/0453* (2013.01)

(56) References Cited

U.S. PATENT DOCUMENTS

2004/0224351 A1  11/2004  Shinohara
2005/0272047 A1  12/2005  Schleifer
2012/0318302 A1  12/2012  Nakayama

FOREIGN PATENT DOCUMENTS

| JP | 07-103984 A | 4/1995 |
| JP | 11-258246 A | 9/1999 |
| JP | 2000-065744 A | 3/2000 |
| JP | 2011-112502 A | 6/2011 |
| JP | 10-267939 A | 10/2016 |

OTHER PUBLICATIONS

Extended European Search Report received in corresponding European Application No. 14785965.6 dated Oct. 4, 2016.
International Search Report of PCT/JP2014/059889.
International Preliminary Report on Patentability received in corresponding International Application No. PCT/JP2014/059889 dated Oct. 29, 2015.

* cited by examiner

AUTOMATIC ANALYZING DEVICE

TECHNICAL FIELD

The present invention relates to an automatic analyzing device for making qualitative and quantitative analyses of biogenic substances such as blood and urine, and particularly relates to an automatic analyzing device for analyzing reaction cuvettes arranged on a circumference of a reaction disk while moving them in a circumferential direction.

BACKGROUND ART

An automatic analyzing device is a device for measuring a reaction between a sample and a reagent by a means such as a photometer, and measuring components contained in the sample. The automatic analyzing device pipettes a sample such as blood, urine, and cerebrospinal fluid from a sample tube or a dedicated container into a reaction cuvette, pipettes a reagent from a reagent bottle into the reaction cuvette, and mixes the sample and the reagent.

In an automatic analyzing device including a disk-shaped reaction disk, reaction cuvettes are arranged in a circumferential direction of the reaction disk. Here, when a specific reagent item easy to stain a reaction cuvette is repeatedly used for a specific reaction cuvette, the reaction cuvette may be stained significantly. In this case, the reaction cuvette becomes unavailable during analytical operation, and analytical throughput decreases.

In the related art, in order to prevent a decrease in analytical throughput attributable to such a significant stain, when a specific reagent item easy to stain a reaction cuvette has been measured, each time after the measurement, the reaction cuvette is rinsed by filling and retaining therein a special detergent for a certain period of time.

In this context, an automatic analyzing device capable of preventing, for each object to be rinsed, a carry-over (carrying over a sample or a reagent to the next analysis) attributable to stains accumulated with a frequency or an hour of use is known (for example, see PTL 1).

CITATION LIST

Patent Literature

PTL 1: JP 2011-112502 A

SUMMARY OF INVENTION

Technical Problem

In an automatic analyzing device as described in PTL 1, reaction cuvettes are rinsed with a predetermined detergent when the frequency or hour of use exceeds a predetermined value.

However, there have been problems that all of the reaction cuvettes become unavailable every time they are rinsed with the predetermined detergent, and that analytical throughput decreases.

An object of the present invention is to provide an automatic analyzing device capable of suppressing a decrease in analytical throughput, while preventing a carry-over attributable to stains accumulated with the frequency or hour of use.

Solution to Problem

In order to achieve the object described above, the present invention includes a retaining mechanism that retains a plurality of reaction cuvettes, a rinse mechanism that rinses the reaction cuvettes with a first detergent and a second detergent, a detergent feeding mechanism that feeds a third detergent to the reaction cuvettes that have been rinsed by the rinse mechanism, a storage unit that stores a use frequency of each reaction cuvette for a specific reagent item, a counting unit that counts and stores in the storage unit the use frequency of each reaction cuvette for the specific reagent item, a determining unit that determines whether the counted use frequency has exceeded a predetermined threshold N1, and a control unit that controls the detergent feeding mechanism such that, in a case where the counted use frequency exceeds the predetermined threshold N1, the reaction cuvettes, which have exceeded the predetermined threshold N1, are soaked with the third detergent only for a period of time equal to or less than a value derived by multiplying a pipetting cycle time, which indicates a period when a sample is pipetted, by the total number of reaction cuvettes and a predetermined integer.

Advantageous Effects of Invention

According to the present invention, a decrease in analytical throughput can be suppressed while preventing a carry-over attributable to stains accumulated with the frequency or hour of use. Problems, configurations, and advantageous effects other than those described above will become apparent by the descriptions of the following embodiments.

BRIEF DESCRIPTION OF DRAWINGS

FIG. 5 is an example of a time chart that describes the operation of the automatic analyzing device according to the first embodiment of the present invention.

FIG. 7 is an example of a time chart that describes an operation of the automatic analyzing device according to the second embodiment of the present invention.

DESCRIPTION OF EMBODIMENTS

First Embodiment

A configuration and an operation of an automatic analyzing device 100A according to a first embodiment of the present invention will be described below using FIGS. 1 to 5.

Figure 1:
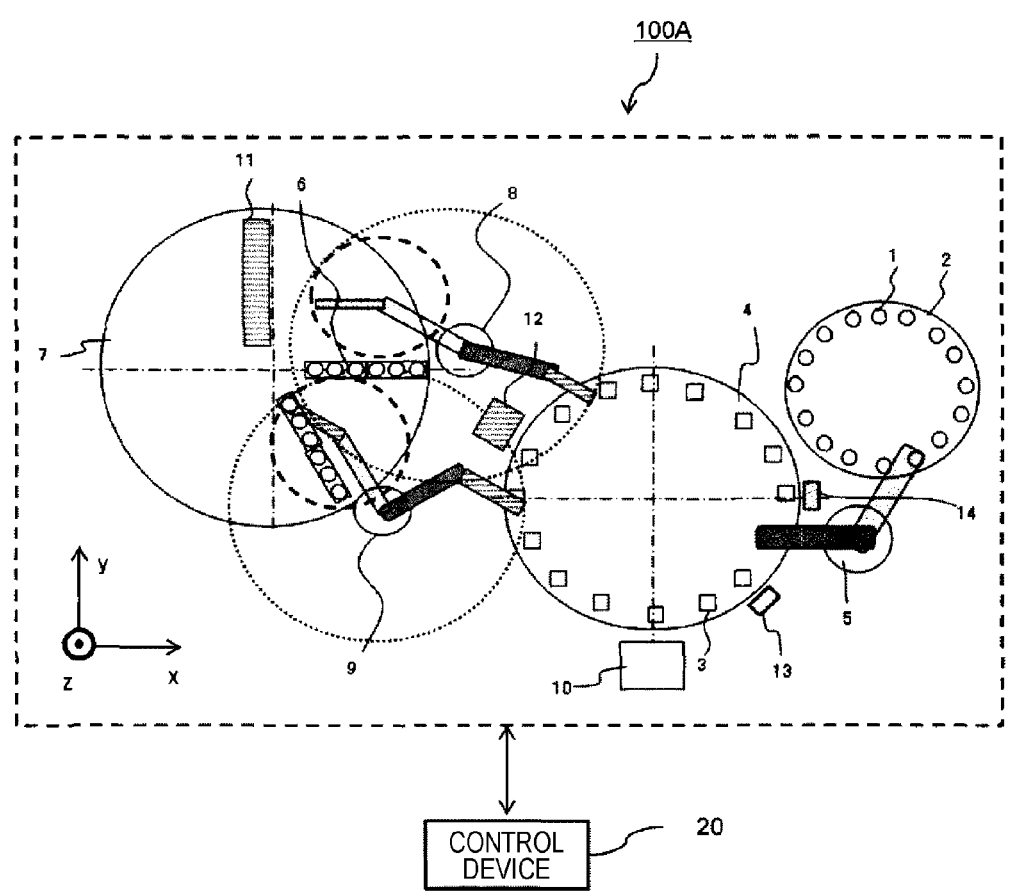
FIG. 1 is a configuration diagram of an automatic analyzing device according to a first embodiment of the present invention.

First, an overall configuration of the automatic analyzing device 100A according to the first embodiment of the present invention will be described using FIG. 1. FIG. 1 is a configuration diagram of the automatic analyzing device 100A according to the first embodiment of the present invention.

The automatic analyzing device 100A mainly includes a sample disk 2, a reaction disk 4, a sample pipetting mechanism 5, a reagent disk 7, an R1 reagent pipetting mechanism 8, an R2/3 reagent pipetting mechanism 9, a photometry part 10, a code reader 11, and a rinse mechanism 12.

The sample disk 2 retains a plurality of sample containers 1 that has contained a sample to be analyzed. The reaction disk 4 retains a plurality of reaction cuvettes 3 for carrying out a reaction and photometry. The sample disk 2 and the reaction disk 4 are rotatable and disk-shaped.

The sample pipetting mechanism 5 suctions the sample from the sample containers 1 retained in the sample disk 2, and pipettes the sample suctioned to the reaction cuvettes 3 retained in the reaction disk 4.

The reagent disk 7 stores and cools a plurality of reagent bottles 6. Each reagent bottle 6 is filled with a first, second, or third reagent that is mixed with the sample and induces a reaction. The reagent disk 7 is rotatable and disk-shaped.

In the present embodiment, a special detergent for rinsing the reaction cuvettes 6 is also filled in the reagent bottles 6, which are disposed in the reagent disk 7. Here, as the special detergent, a plurality of types of detergents different in rinsing effects (acid and alkaline strength) can be set. In the present embodiment, an acid-based detergent (pH=2 to 3, or lower) and an alkali-based detergent (pH=12 to 14, or higher) are used as the special detergent.

The R1 reagent pipetting mechanism 8 pipettes the reagent from the reagent bottles 6 for the first reagent to the reaction cuvettes 3 retained in the reaction disk 4. The R1 reagent pipetting mechanism 8 discharges the special detergent to the reaction cuvettes 3 at a predetermined timing and carries out rinsing. Details of a rinsing operation using the special detergent will be described later using FIGS. 4 and 5.

The R2/3 reagent pipetting mechanism 9 pipettes the reagent from the reagent bottles 6 for the second or third reagent to the reaction cuvettes 3 retained in the reaction disk 4. The photometry part 10 carries out photometry of light transmitted through the reaction cuvettes 3. The code reader 11 reads an identification code provided to the reagent bottles 6.

The rinse mechanism 12 includes a discharge nozzle that discharges rinse water and the detergent, a suction nozzle that suctions, for example, a reaction liquid, and the like. The rinse mechanism 12 rinses the reaction cuvettes 3 with the rinse water and the detergent. Details of a configuration of the rinse mechanism 12 will be described later using FIGS. 2A and 2B.

An R1 stirring mechanism 13 stirs a mixture of the sample and the reagent that are reacting in the reaction cuvettes 3 on the reaction disk 4. An R2/3 stirring mechanism 14 has a similar function.

A control device 20 includes a computer and the like, and controls an operation of each table (sample disk 2, reaction disk 4, reagent disk 7) and each mechanism (sample pipetting mechanism 5, R1 reagent pipetting mechanism 8, and the like).

The reaction disk 4, the rinse mechanism 12, and the R1 reagent pipetting mechanism 8 correspond to a retaining mechanism, the rinse mechanism, and a detergent feeding mechanism, respectively.

Figure 2A:
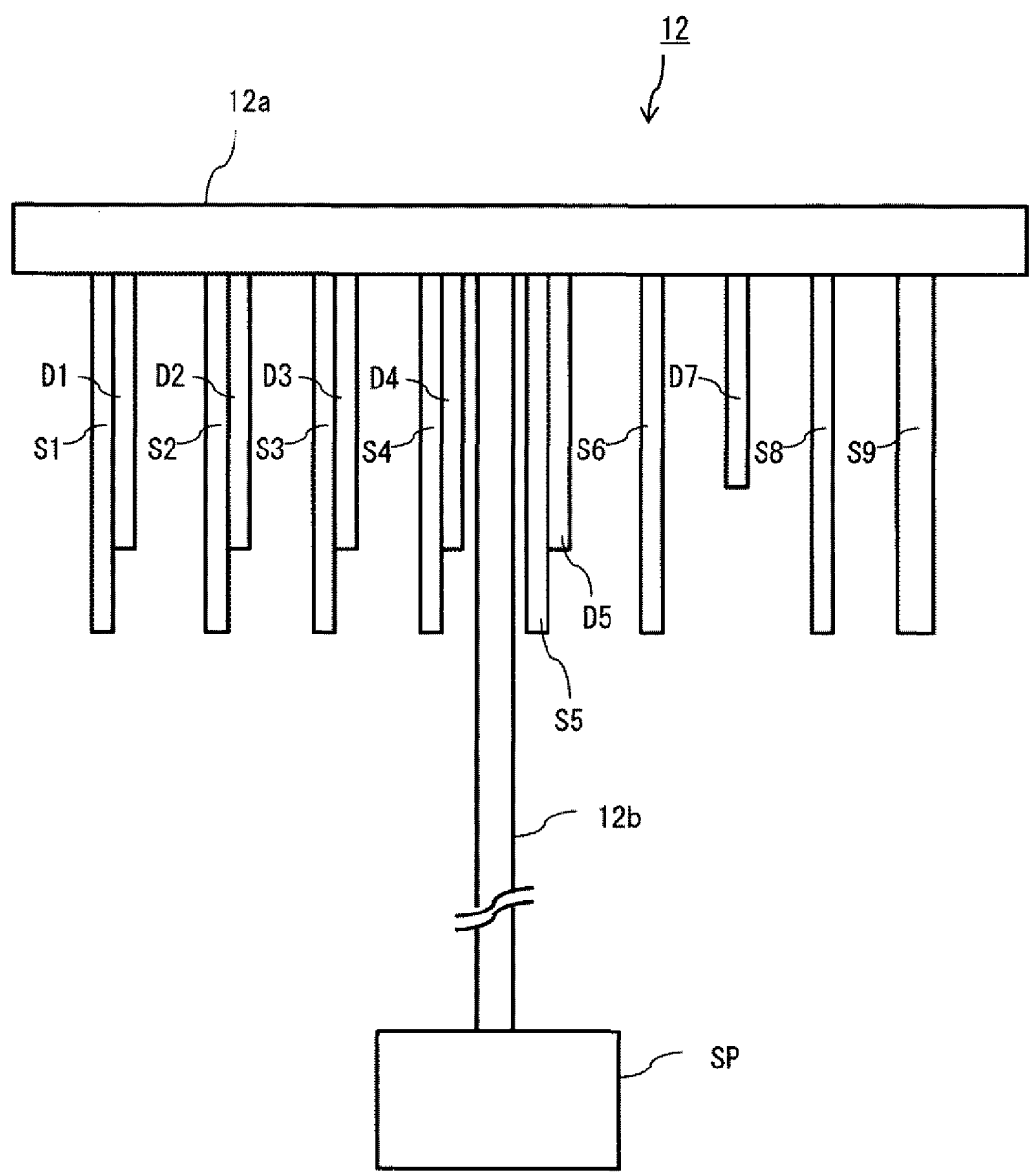
FIG. 2A is a configuration diagram (front view) of a rinse mechanism used for the automatic analyzing device according to the first embodiment of the present invention.

Next, a configuration of the rinse mechanism 12 used for the automatic analyzing device 100A according to the first embodiment of the present invention will be described using FIG. 2A. FIG. 2A is a configuration diagram (front view) of the rinse mechanism 12 used for the automatic analyzing device 100A according to the first embodiment of the present invention.

The rinse mechanism 12 includes an arm 12a, suction nozzles S1 to S6 and S9, discharge nozzles D1 to D5 and D7, a supporting unit 12b, a syringe pump SP, and the like.

The suction nozzle S1 and the discharge nozzle D1 are disposed adjacent to each other on the arm 12a. The suction nozzles S2 to S5 and the discharge nozzles D2 to D5 are similarly disposed on the arm 12a.

The suction nozzles S (S1 to S9) suction a liquid such as the reaction liquid and the rinse water from the reaction cuvettes 3 by the syringe pump. The discharge nozzles D (D1 to D7) discharge a liquid such as the rinse water and the detergent to the reaction cuvettes 3 by the syringe pump.

The diameters of the suction nozzles S1 to S8 and the discharge nozzles D1 to D7 are substantially the same, but the diameter of the suction nozzle S9 is larger. The reason is to completely suction the rinse water left in the reaction cuvettes 3. However, instead of making the diameter of the suction nozzle S9 larger, an attachment with a larger diameter may be attached. Details of an operation of the rinse mechanism 12 will be described later using FIG. 4.

Figure 2B:
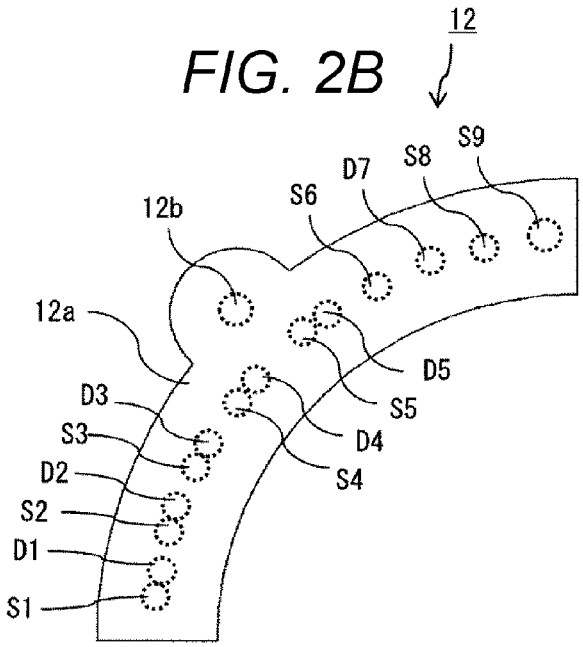
FIG. 2B is a configuration diagram (top view) of the rinse mechanism used for the automatic analyzing device according to the first embodiment of the present invention.

Next, the configuration of the rinse mechanism 12 used for the automatic analyzing device 100A according to the first embodiment of the present invention will be described using FIG. 2B. FIG. 2B is a configuration diagram (top view) of the rinse mechanism 12 used for the automatic analyzing device 100A according to the first embodiment of the present invention.

The arm 12a is substantially one-quarter ring-shaped. The suction nozzles S (S1 to S9) and the discharge nozzles D (D1 to D7) are disposed in an arc-shape on the lower surface of the arm 12a.

Specifically, a set of the suction nozzle S1 and the discharge nozzle D1, a set of the suction nozzle S2 and the discharge nozzle D2, a set of the suction nozzle S3 and the discharge nozzle D3, a set of the suction nozzle S4 and the discharge nozzle D4, a set of the suction nozzle S5 and the discharge nozzle D5, the suction nozzle S6, the discharge nozzle D7, the suction nozzle S8, and the suction nozzle S9 are disposed at a certain distance in a circumferential direction.

Rotation of the reaction disk 4 is controlled such that the reaction cuvettes 3 which have completed a measurement are positioned below the suction nozzles S and the discharge nozzles D (in the direction of z (−)). The supporting unit 12b is fixed in the center of the arm 12a in the circumferential direction.

Figure 3:
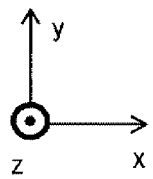
FIG. 3 is a diagram that describes a function of a control device used for the automatic analyzing device according to the first embodiment of the present invention.
Figure 3:
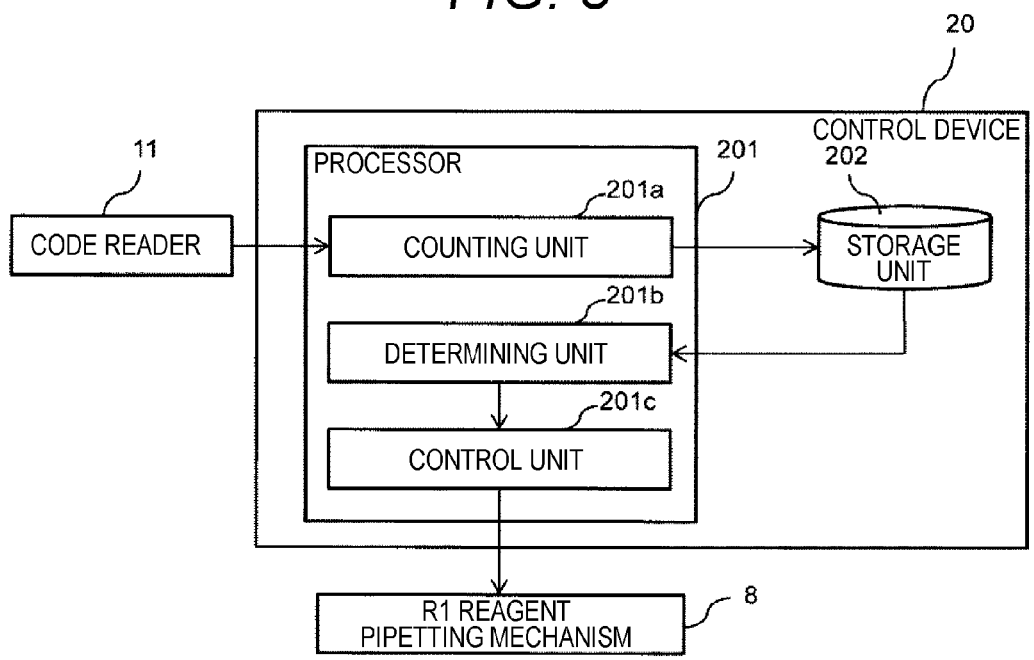

Next, a function of the control device 20 used for the automatic analyzing device 100A according to the first embodiment of the present invention will be described using FIG. 3. FIG. 3 is a diagram that describes the function of the control device 20 used for the automatic analyzing device 100A according to the embodiment of the present invention.

The control device 20 includes a processor 201 and a storage unit 202 (hard disk, memory, and the like). The processor 201 functions as a counting unit 201a, a determining unit 201b, and a control unit 201c.

Specifically, the counting unit 201a counts and stores in the storage unit 202 the use frequency of each reaction cuvette 3 for a specific reagent item based on the identification code of the reagent bottles 6, read by the code reader 11. The determining unit 201b determines whether the use frequency of each reaction cuvette 3 for the specific reagent item exceeds a predetermined threshold.

In a case where the counted use frequency exceeds the predetermined threshold, the control unit 201c controls the R1 reagent pipetting mechanism 8 so as to soak with the special detergent only for a period derived by multiplying a pipetting cycle time, which indicates a period when a sample is pipetted, by the total number of reaction cuvettes and a predetermined integer. The predetermined threshold can be input from an input device (keyboard, mouse, and the like) connected to the control device 20. The predetermined threshold is equal to or greater than two.

Figure 4:
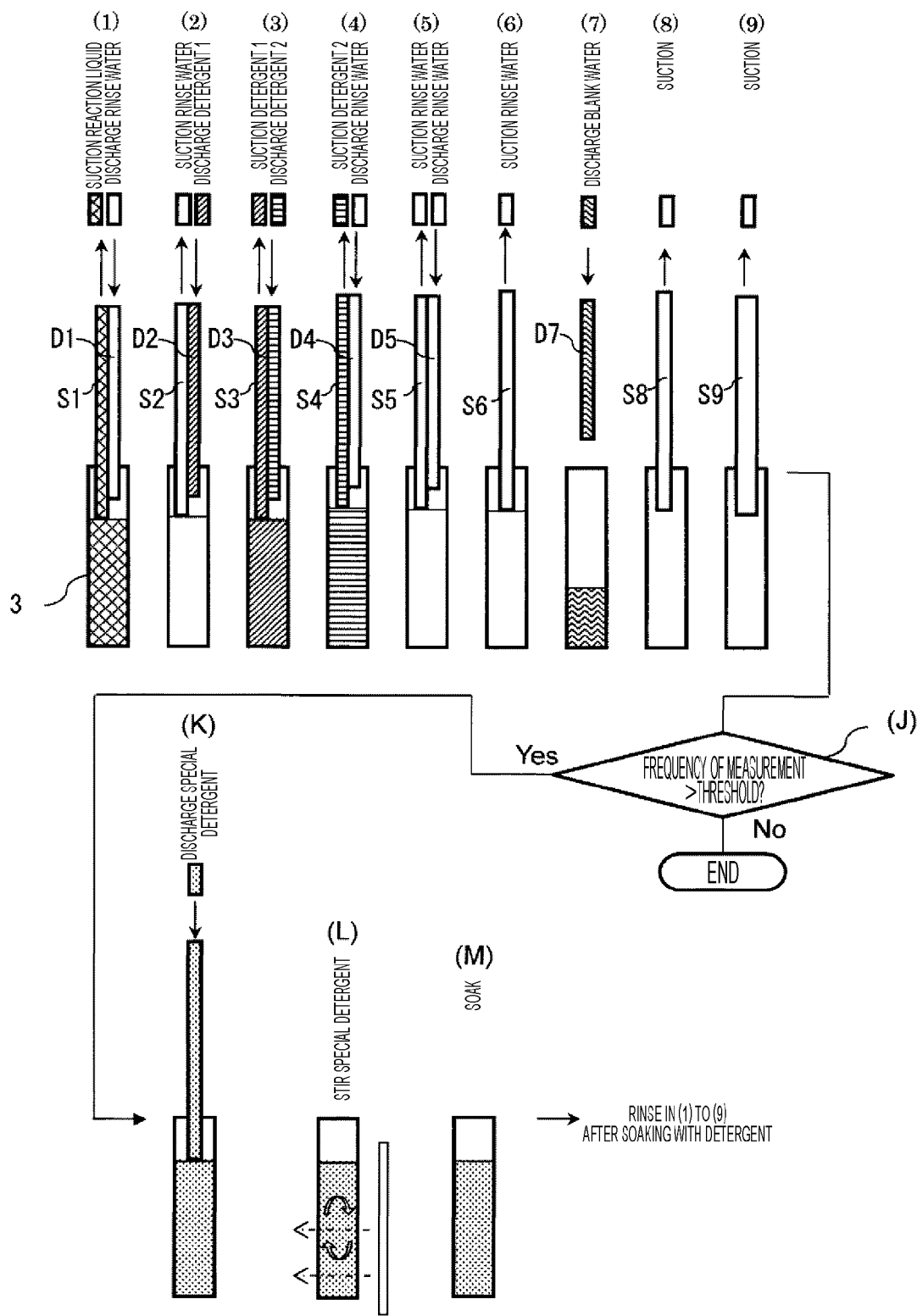
FIG. 4 is a diagram that describes an operation of the automatic analyzing device according to the first embodiment of the present invention.

Next, an operation of the automatic analyzing device 100A according to the first embodiment of the present invention will be described using FIG. 4. FIG. 4 is a diagram that describes the operation of the automatic analyzing device 100A according to the first embodiment of the present invention.

First, the operation of the rinse mechanism 12 will be described for each pipetting cycle time, which indicates a period when the liquid (rinse water, detergent, and the like) is pipetted into the reaction cuvettes.

(1) In a first cycle, the rinse mechanism 12 suctions the reaction liquid from the reaction cuvettes 3 by the suction nozzle S1. Next, the rinse mechanism 12 discharges the rinse water into the reaction cuvettes 3 by the discharge nozzle D1. The rinse water is deionized water (ion-exchange water).

(2) In a second cycle, the rinse mechanism 12 suctions the rinse water from the reaction cuvettes 3 by the suction nozzle S1. Next, the rinse mechanism 12 discharges a detergent 1 into the reaction cuvettes 3 by the discharge nozzle D2. The detergent 1 is an alkali-based detergent.

(3) In a third cycle, the rinse mechanism 12 suctions the detergent 1 from the reaction cuvettes 3 by the suction nozzle S3. Next, the rinse mechanism 12 discharges a detergent 2 into the reaction cuvettes 3 by the discharge nozzle D3. The detergent 2 is an acid-based detergent.

(4) In a fourth cycle, the rinse mechanism 12 suctions the detergent 2 from the reaction cuvettes 3 by the suction nozzle S4. Next, the rinse mechanism 12 discharges the rinse water into the reaction cuvettes 3 by the discharge nozzle D4.

(5) In a fifth cycle, the rinse mechanism 12 suctions the rinse water from the reaction cuvettes 3 by the suction nozzle S5. Next, the rinse mechanism 12 discharges the rinse water by the discharge nozzle D5.

(6) In a sixth cycle, the rinse mechanism 12 suctions the rinse water from the reaction cuvettes 3 by the suction nozzle S6.

(7) In a seventh cycle, the rinse mechanism 12 discharges blank water by the discharge nozzle D7. The blank water is deionized water (ion-exchange water). The blank water is used to keep a condition obtained by rinsing with the detergents 1 and 2. Therefore, the amount of the blank water discharged into the reaction cuvettes 3 in the seventh cycle is less than that of the rinse water discharged into the reaction cuvettes 3 in other cycles.

(8) In an eighth cycle, the rinse mechanism 12 suctions the blank water from the reaction cuvettes 3 by the suction nozzle S8.

(9) In a ninth cycle, the rinse mechanism 12 suctions the blank water from the reaction cuvettes 3 by the suction nozzle S9. In the eighth and ninth cycles, the blank water is continuously suctioned from the reaction cuvettes 3. Thus, the blank water in the reaction cuvettes 3 is almost completely suctioned.

As described in (1) to (9) above, a normal rinsing operation is completed. Next, a special rinsing operation by the R1 reagent pipetting mechanism 8 and the like will be described.

(J) When the normal rinsing operation is completed, the control device 20 determines, for the reaction cuvettes 3 which have completed rinsing by the rinse mechanism 12, whether the frequency of measurement for the specific reagent item (such as hemoglobin Alc (HbAlc) difficult to remove) exceeds a predetermined threshold.

When the frequency of measurement does not exceed the predetermined threshold, the control device 20 finishes rinsing of the reaction cuvettes 3. Then, the reaction cuvettes 3 that have completed rinsing are used for the next measurement.

On the other hand, when the frequency of measurement exceeds the predetermined threshold, the control device 20 carries out, as described below, a special rinsing operation.

(K) When the frequency of measurement exceeds the predetermined threshold, the R1 reagent pipetting mechanism 8 suctions the special detergent retained in the reagent disk 7 and discharges the special detergent into the reaction cuvettes 3. In the present embodiment, the R1 reagent pipetting mechanism 8 suctions and discharges the special detergent. However, the R2/3 reagent pipetting mechanism 9 may suction and discharge the special detergent.

(L) The R1 stirring mechanism 13 stirs the special detergent in the reaction cuvettes. As a result, the rinsing effect increases.

(M) Then, the reaction cuvettes 3 are soaked with the special detergent for a certain period of time. The time for soaking with the special detergent is, in (1) to (9), longer than the time for the rinse mechanism 12 to rinse the reaction cuvettes 3. Although not always required, it is preferable, as described above, to stir the special detergent while the reaction cuvettes are soaked with the special detergent.

Figure 5:
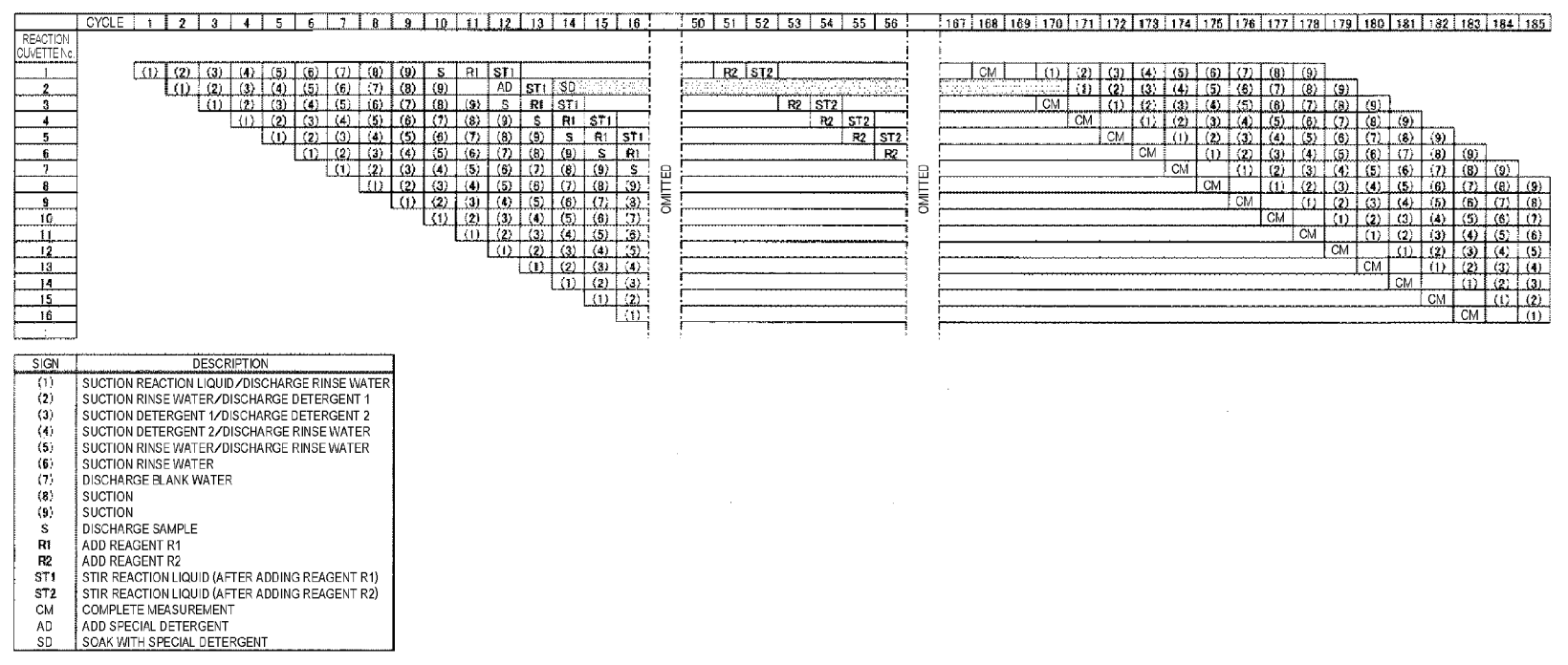

Next, the operation of the automatic analyzing device 100A according to the first embodiment of the present invention will be described using FIG. 5. FIG. 5 is an example of a time chart that describes the operation of the automatic analyzing device 100A according to the first embodiment of the present invention. For ease of description, consecutive numbers (No. 1, No. 2, . . . ) are assigned to a plurality of reaction cuvettes 3 arranged on the reaction disk 4 in a circumferential direction (for example, clockwise).

A rinsing operation in a case where the frequency of measurement for the specific reagent item (for example, HbAlc) exceeds the predetermined threshold at a No. 2 reaction cuvette 3, and does not exceed the predetermined threshold at the other reaction cuvettes will be described below as an example.

No. 1 Reaction Cuvette

First, a rinsing operation in a No. 1 reaction cuvette 3 will be described using FIG. 5. As described using FIG. 4, the normal rinsing operation is carried out in the first to ninth cycles.

Here, in the No. 1 reaction cuvette 3, the frequency of measurement for the specific reagent item does not exceed the predetermined threshold. Therefore, in a 10th cycle, the sample pipetting mechanism 5 suctions the sample from the sample containers 1 retained in the sample disk 2, and pipettes the sample suctioned to the No. 1 reaction cuvette 3.

In an 11th cycle, the R1 reagent pipetting mechanism 8 suctions a reagent R1 from the reagent bottles 6 for the first reagent and pipettes (adds) the reagent R1 suctioned to the No. 1 reaction cuvette 3.

In a 12th cycle, the R1 stirring mechanism 13 stirs the reaction liquid in the No. 1 reaction cuvette.

Then, in a 51st cycle, the R2/3 reagent pipetting mechanism 9 suctions a reagent R2 from the reagent bottles 6 for a second reagent and pipettes the reagent R2 suctioned to the No. 1 reaction cuvette 3.

In a 52nd cycle, the R2/3 stirring mechanism 14 stirs the reaction liquid in the No. 1 reaction cuvette.

Then, in a 168th cycle, the photometry part 10 completes photometry of light transmitted through the No. 1 reaction cuvette 3.

In 170th to 178th cycles, processing in (1) to (9) is executed. Accordingly, the normal rinsing operation is completed.

No. 2 Reaction Cuvette

Next, a rinsing operation in a No. 2 reaction cuvette 3 will be described using FIG. 5. In the second to 10th cycles, a normal rinsing operation is carried out. The timing for initiating rinsing of the No. 2 reaction cuvette 3 is one cycle behind compared with the No. 1 reaction cuvette 3.

Here, in the No. 2 reaction cuvette 3, the frequency of measurement for the specific reagent item exceeds the predetermined threshold. Therefore, in the 12th cycle, the R1 reagent pipetting mechanism 8 suctions the special detergent retained in the reagent disk 7 and discharges the special detergent to the No. 2 reaction cuvette 3.

In a 13th cycle, the R1 stirring mechanism 13 stirs the special detergent in the No. 2 reaction cuvette.

Then, in 14th to 170th cycles, the No. 2 reaction cuvette is soaked with the special detergent.

In 171st to 178th cycles, the processing described in (1) to (9) is executed.

In the present embodiment, as with the No. 1 reaction cuvette 3, when only the normal rinsing is carried out, an interval, at which the sample is pipetted, is 169 cycles. In an example of FIG. 5, after a sample is pipetted in the 10th cycle, the next sample can be pipetted in a 179th cycle.

On the other hand, as with the No. 2 reaction cuvette 3, when the special rising is carried out once, an interval, at which the sample is pipetted, is 169+169=169×2 cycles. Here, the time for soaking with the special detergent is the time from a cycle when the detergent is discharged to a cycle when soaking is completed. In the No. 2 reaction cuvette 3 illustrated in FIG. 5, the time for soaking with the special detergent is the time from the 12th cycle to the 170th cycle. That is, the time for soaking with the special detergent is 159 cycles, and pipetting cycle×total number of reaction cuvettes−(rinse cycle+free cycle) of the automatic analyzing device 100A. In the present embodiment, the number of reaction cuvettes is 169, pipetting cycle is 3.6 seconds, rinse cycle is nine, and free cycle is one. Therefore, the time for soaking is 3.6×169−(9+1)=572.4 seconds.

The time for soaking with the special detergent may be pipetting cycle×total number of reaction cuvettes×integer−(rinse cycle+free cycle) of the automatic analyzing device 100A. Here, the rinse and free cycles differ for each automatic analyzing device. Therefore, the time for soaking with the special detergent is represented as pipetting cycle×total number of reaction cuvettes×an integer INT1−an integer INT2. In other words, the time for soaking with the special detergent is set equal to or less than a value derived from pipetting cycle×total number of reaction cuvettes×integer. The time for soaking with the special detergent may be designated by inputting an integer used in this formula from the input device. Here, an integer means an integer equal to or greater than 1. On the other hand, a lower limit is preferably 10 times or more the pipetting cycle. Therefore, it is preferable that the control unit 201*c* control the detergent feeding mechanism such that reaction cuvettes, which have exceeded the predetermined threshold, are soaked with the special detergent for a period 10 times or longer the pipetting cycle time.

As described above, according to the present embodiment, the time before the next sample is pipetted after the normal rinsing is carried out, following the special rinsing can be shortened. Thus, even when the special rinsing is carried out, a decrease in analytical throughput can be suppressed. In addition, a carry-over attributable to stains accumulated with the frequency or hour of use by the special rinsing can be prevented.

Second Embodiment

Next, a configuration and an operation of an automatic analyzing device 100B according to a second embodiment of the present invention will be described using FIGS. 6 and 7.

First, an overall configuration of the automatic analyzing device 100B according to the second embodiment of the present invention will be described using FIG. 6. FIG. 6 is a configuration diagram of the automatic analyzing device 100B according to the second embodiment of the present invention. In FIG. 6, sections identical to those in FIG. 1 bear identical signs.

Figure 6:
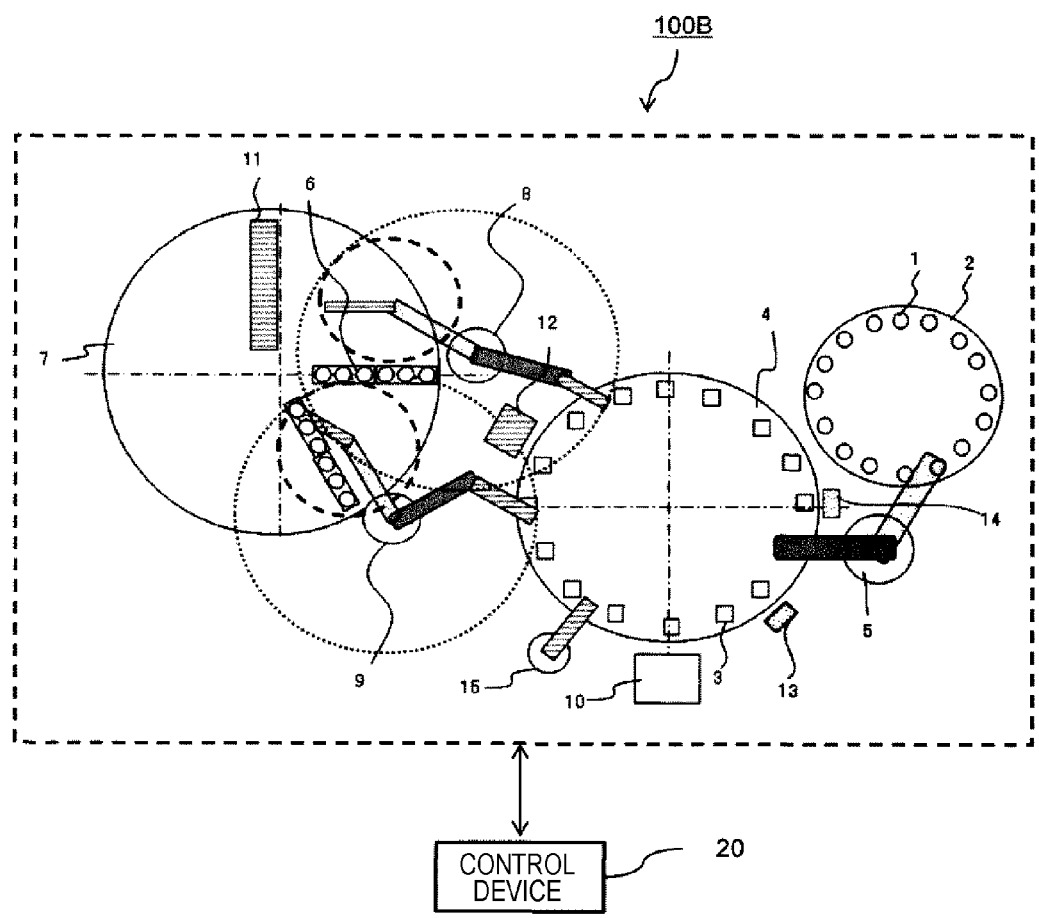
FIG. 6 is a configuration diagram of an automatic analyzing device according to a second embodiment of the present invention.

In FIG. 6, a difference from FIG. 1 is that the automatic analyzing device 100B includes a nozzle 15 dedicated for a special detergent. In the present embodiment, the special detergent is disposed at a place other than a reagent disk 7. Specifically, a tank for storing the special detergent may be provided, for example, near the nozzle 15 dedicated for a special detergent.

Next, an operation of the automatic analyzing device 100B according to the second embodiment of the present invention will be described using FIG. 7. FIG. 7 is an example of a time chart that describes the operation of the automatic analyzing device 100B according to the second embodiment of the present invention.

Figure 7:
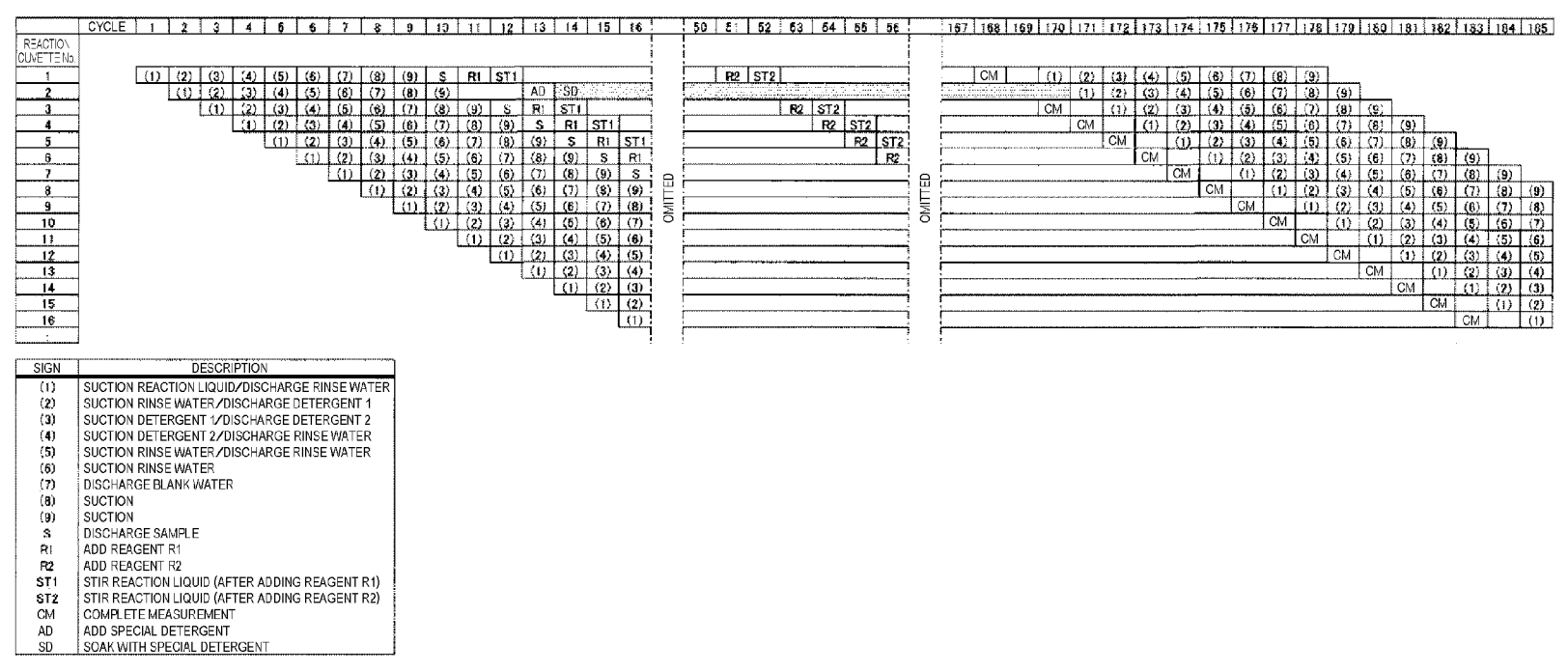

In FIG. 7, a difference from FIG. 5 is timing for rinsing a No. 2 reaction cuvette 3 with the special detergent. Specifically, in the present embodiment, the special detergent is, in a 13th cycle, discharged from the nozzle 15 dedicated for a special detergent into the No. 2 reaction cuvette 3.

As described above, according to the present embodiment, the timing for discharging the special detergent by the nozzle 15 dedicated for a special detergent can be appropriately changed.

Modification 1

A sample pipetting mechanism 5 may discharge a special detergent into reaction cuvettes 3. In this case, the special detergent is filled in similar containers to sample containers 1 and disposed in a sample disk 2.

According to the present modification, timing for discharging the special detergent by the sample pipetting mechanism 5 can be appropriately changed.

In the present modification, an automatic analyzing device is assumed, where the sample containers 1 are disposed in the sample disk 2. However, in a case of an automatic analyzing device where the sample containers 1 are disposed in a rack, the special detergent is disposed in the rack.

Modification 2

In the first and second embodiments, a counting unit 201a counts and stores in a storage unit 202 a use frequency of each reaction cuvette 3 for a specific reagent item. Here, when predetermined operations are carried out, such as when the reaction cuvettes 3 are rinsed with the special detergent and when the reaction cuvettes 3 are exchanged, the use frequency stored in the storage unit 202 may be reset.

After these predetermined operations are carried out, a count is reset even when the use frequency of each reaction cuvette for the specific reagent item is equal to or below a threshold.

Modification 3

A plurality of thresholds of a use frequency for a specific reagent item, which serves as a criterion to determine whether to carry out rinsing with a special detergent, may be provided. For example, in a case where two thresholds are set at N1 and N2 (N1<N2), when the use frequency exceeds N1, a special rinsing is not carried out for reaction cuvettes, the use frequency of which exceeds N1, during a measurement. After the measurement, when there is not a request for a new measurement, the special rinsing will be carried out. When there is a request for a new measurement after the measurement, the special rinsing is not carried out, and a measurement is made in response to the request for the new measurement, using the reaction cuvettes, the use frequency of which has exceeded N1. On the other hand, in a case where the use frequency has exceeded N2, for the reaction cuvettes, the use frequency of which has exceeded N2, the special rinsing is carried out with the special detergent and the new measurement is not assigned even when there is a request for the new measurement after the measurement.

Other Modifications

A frequency of rinsing with a special detergent for each reaction cuvette 3 may be stored and displayed on a display device. Timing for exchanging reaction cuvettes and a threshold for the timing for the exchange may be made changeable at the input device via a screen displayed on a display device.

Instead of storing the frequency of rising with the special detergent, a total use frequency of a specific reagent item may be stored and made a threshold.

The present invention is not limited to the embodiments described above, but includes a variety of modifications. For example, the embodiments described above have been described in detail in order to describe the prevent invention clearly, and are not necessarily limited to those including all of the configurations that have been described. A part of a configuration in an embodiment can be replaced with a configuration in another embodiment, and a configuration of another embodiment can also be added to a configuration of an embodiment. For a part of a configuration of each embodiment, other configurations can be added, deleted, or substituted.

REFERENCE SIGNS LIST

1 Sample container
2 Sample disk
3 Reaction cuvette
4 Reaction disk
5 Sample pipetting mechanism
6 Reagent bottle
7 Reagent disk
8 R1 reagent pipetting mechanism
9 R2/3 reagent pipetting mechanism
10 Photometry part
11 Code reader
12 Rinse mechanism
13 R1 stirring mechanism
14 R2/3 stirring mechanism
15 Nozzle dedicated for special detergent
20 Control device
201 Processor
201a Counting unit
201b Determining unit
201c Control unit
202 Storage unit
100A, 100B Automatic analyzing device

The invention claimed is:

1. An automatic analyzing device comprising:
a retaining mechanism that retains a plurality of reaction cuvettes;
a reagent disk that retains a plurality of reagent containers containing a plurality of types of reagents;
a rinse mechanism including a plurality of suction nozzles and a plurality of discharge nozzles that rinses the reaction cuvettes with a first detergent and a second detergent;
a detergent feeding mechanism disposed adjacent to the retaining mechanism configured to dispense a third detergent to one or more reaction cuvettes;
a code reader that reads code information disposed on each of the plurality of the reagent containers; and
a control unit coupled to the rinse mechanism, the detergent feeding mechanism, and the code reader, that is programmed to:
read code information from one or more of the reagent containers and determine a use frequency of each type of reagent based on the read code information,
determine whether the use frequency exceeds a predetermined threshold N1,
control the rinse mechanism to rinse each reaction cuvette with a first detergent and a second detergent,
upon determining that the use frequency exceeds the predetermined threshold N1, control the detergent feeding mechanism to dispense the third detergent into only each of the reaction cuvettes that have exceeded the predetermined threshold N1 and control the rinse mechanism to rinse the reaction cuvettes that have exceeded the predetermined threshold N1 again only after a period of time equal to a value derived by multiplying a pipetting cycle time, which indicates a period of time when a sample is pipetted, by the total number of the plurality of reaction cuvettes and a predetermined integer, has lapsed.

2. The automatic analyzing device according to claim 1, wherein the detergent feeding mechanism comprises a nozzle dedicated for the third detergent, provided separately from a reagent pipetting mechanism configured to pipette a reagent from reagent bottles to the reaction cuvettes and a sample pipetting mechanism configured to pipette a sample from sample containers to the reaction cuvettes.

3. The automatic analyzing device according to claim 1, wherein the retaining mechanism is a rotatable disk.

4. The automatic analyzing device according to claim 1, wherein the threshold N1 is equal to or greater than 2.

5. The automatic analyzing device according to claim 1, wherein the control unit controls the detergent mechanism such that the reaction cuvettes, which have exceeded the predetermined threshold N1, are soaked with the third detergent for a period 10 times or longer the pipetting cycle time.

6. The automatic analyzing device according to claim 1, wherein the third detergent is stirred while the reaction cuvettes, which have exceeded the predetermined threshold N1, are soaked with the third detergent.

7. The automatic analyzing device according to claim 1, wherein the plurality of the suction nozzles and the plurality of the discharge nozzles of the rinse mechanism are disposed on an arm having a curved shape, wherein, of the plurality of discharge nozzles, a first discharge nozzle discharges rinse water, a second discharge nozzle discharges the first detergent, a third discharge nozzle discharges the second detergent, a fourth discharge nozzle discharges deionized water, and wherein one of the suction nozzles of the plurality of suction nozzles has a greater diameter than the other plurality of suction nozzles.

8. The automatic analyzer according to claim 1, wherein the rinse mechanism is configured to rinse the reaction cuvettes with a second detergent different from the first detergent.

9. The automatic analyzer according to claim 1, wherein the rinse mechanism is configured to rinse the reaction cuvettes with a second detergent that is acid-based and different from the first detergent, and a third detergent that is alkali-based and different from the first detergent and the second detergent.

* * * * *